(12) United States Patent
Baba et al.

(10) Patent No.: US 9,612,109 B2
(45) Date of Patent: Apr. 4, 2017

(54) INNER DIAMETER MEASURING DEVICE

(71) Applicant: IHI Corporation, Koto-ku, Tokyo (JP)

(72) Inventors: Michiko Baba, Tokyo (JP); Kiyofumi Fujimura, Tokyo (JP); Toshihiro Hayashi, Tokyo (JP); Norimasa Taga, Tokyo (JP)

(73) Assignee: IHI Corporation, Tokyo (JP)

( * ) Notice: Subject to any disclaimer, the term of this patent is extended or adjusted under 35 U.S.C. 154(b) by 284 days.

(21) Appl. No.: 14/377,236

(22) PCT Filed: Feb. 7, 2013

(86) PCT No.: PCT/JP2013/053591
§ 371 (c)(1),
(2) Date: Aug. 7, 2014

(87) PCT Pub. No.: WO2013/118913
PCT Pub. Date: Aug. 15, 2013

(65) Prior Publication Data
US 2015/0009322 A1 Jan. 8, 2015

(30) Foreign Application Priority Data

Feb. 9, 2012 (JP) ................................ 2012-026047

(51) Int. Cl.
G01B 11/02 (2006.01)
G01B 11/12 (2006.01)
(Continued)

(52) U.S. Cl.
CPC .............. G01B 11/12 (2013.01); G01B 11/24 (2013.01); G02B 5/001 (2013.01); G02B 23/2423 (2013.01); G01N 2021/9544 (2013.01)

(58) Field of Classification Search
CPC ......... G01B 11/24; G01B 11/12; G01B 11/00; G01N 21/00
(Continued)

(56) References Cited

U.S. PATENT DOCUMENTS 1,664,851 A 4/1928 Class
1,721,524 A 7/1929 Moore
(Continued)

FOREIGN PATENT DOCUMENTS

EP 0076144 A2 4/1983
EP 0373514 A1 6/1990
(Continued)

OTHER PUBLICATIONS

Office action mailed Mar. 22, 2016 in co-pending U.S. Appl. No. 14/377,238.
(Continued)

Primary Examiner — Tarifur Chowdhury
Assistant Examiner — Isiaka Akanbi
(74) Attorney, Agent, or Firm — Nields, Lemack & Frame, LLC

(57) ABSTRACT

An inner diameter measuring device for measuring a shape of an inner surface of a cylindrical member, comprising an image pickup unit (2) disposed on a base end side of a frame unit (10) and for picking up an image of a forward end side, a cone mirror unit (30) provided on a forward end side of the frame unit and having a cone mirror (29) with a conical reflection surface at a forward end, and a laser beam emitting unit (14) for emitting a laser beam (17) toward a forward end of the cone mirror, wherein the cone mirror unit can be replaced by another cone mirror unit having a cone mirror with a different vertical angle to suit measuring condition.

5 Claims, 6 Drawing Sheets

(51) Int. Cl.
*G01B 11/24* (2006.01)
*G02B 5/00* (2006.01)
*G02B 23/24* (2006.01)
*G01N 21/954* (2006.01)

(58) Field of Classification Search
USPC .............................. 356/150, 635, 630, 626
See application file for complete search history.

(56) References Cited

U.S. PATENT DOCUMENTS

| | | | |
|---|---|---|---|
| 2,822,620 A | 2/1958 | Ulfeldt | |
| 3,028,496 A | 4/1962 | Kennard et al. | |
| 3,247,732 A | 4/1966 | Barnhart | |
| 3,436,967 A | 4/1969 | Post | |
| 3,771,350 A | 11/1973 | Romans | |
| 4,045,877 A | 9/1977 | Rutter | |
| 4,382,338 A | 5/1983 | Possati et al. | |
| 4,536,963 A | 8/1985 | Yamamoto et al. | |
| 4,631,834 A | 12/1986 | Hayashi et al. | |
| 4,872,269 A | 10/1989 | Sattmann | |
| 4,899,277 A * | 2/1990 | Iizuka ................. | E21B 47/0002 356/241.1 |
| 4,934,813 A * | 6/1990 | Yaginuma ............ | G01N 21/954 356/241.1 |
| 4,937,524 A | 6/1990 | Fasnacht et al. | |
| 4,967,092 A | 10/1990 | Fraignier et al. | |
| 5,083,384 A | 1/1992 | Possati et al. | |
| 5,095,634 A | 3/1992 | Overlach et al. | |
| 5,224,274 A | 7/1993 | Blaiklock | |
| 5,259,119 A | 11/1993 | Yoshioka et al. | |
| 5,808,250 A | 9/1998 | Torii et al. | |
| 5,933,231 A | 8/1999 | Bieman et al. | |
| 6,243,962 B1 | 6/2001 | Brock | |
| 6,249,007 B1 | 6/2001 | Gooch et al. | |
| 6,427,353 B1 | 8/2002 | Nelson et al. | |
| 6,931,149 B2 | 8/2005 | Hagene et al. | |
| 8,033,032 B2 | 10/2011 | Fujikawa et al. | |
| 8,841,603 B1 | 9/2014 | Blanton et al. | |
| 8,842,297 B2 | 9/2014 | Størksen et al. | |
| 9,145,924 B2 | 9/2015 | Baba et al. | |
| 9,372,061 B2 | 6/2016 | Baba et al. | |
| 9,372,073 B2 | 6/2016 | Baba et al. | |
| 9,410,795 B2 | 8/2016 | Baba et al. | |
| 9,429,409 B2 | 8/2016 | Baba et al. | |
| 9,470,509 B2 | 10/2016 | Baba et al. | |
| 2003/0198374 A1 | 10/2003 | Hagene et al. | |
| 2004/0114793 A1 | 6/2004 | Bondurant | |
| 2006/0044089 A1 | 3/2006 | Kang et al. | |
| 2006/0112577 A1 | 6/2006 | Jones | |
| 2006/0283037 A1 | 12/2006 | Galle | |
| 2008/0105067 A1 | 5/2008 | Frey | |
| 2009/0144999 A1 | 6/2009 | Lau | |
| 2010/0005676 A1 | 1/2010 | Fujikawa et al. | |
| 2010/0060904 A1 | 3/2010 | Keightley et al. | |
| 2010/0110448 A1 | 5/2010 | Johnson et al. | |
| 2011/0080588 A1 | 4/2011 | Segall | |
| 2015/0000465 A1 | 1/2015 | Baba et al. | |
| 2015/0002836 A1 | 1/2015 | Baba et al. | |
| 2015/0007440 A1 | 1/2015 | Baba et al. | |
| 2015/0015695 A1 | 1/2015 | Baba et al. | |
| 2015/0015873 A1 | 1/2015 | Baba et al. | |
| 2015/0020395 A1 | 1/2015 | Baba et al. | |
| 2015/0131109 A1 | 5/2015 | Baba et al. | |

FOREIGN PATENT DOCUMENTS

| | | | |
|---|---|---|---|
| EP | 1434076 A1 | 6/2004 | |
| EP | 2818825 A1 | 12/2014 | |
| FR | 2730304 A1 | 8/1996 | |
| GB | 1388475 A | 3/1975 | |
| JP | 50-159355 A | 12/1975 | |
| JP | 57-22501 A | 2/1982 | |
| JP | 58-66809 A | 4/1983 | |
| JP | 59-187155 A | 10/1984 | |
| JP | 61-144551 A | 7/1986 | |
| JP | 61-282659 A | 12/1986 | |
| JP | 63-55441 A | 3/1988 | |
| JP | 63-159708 A | 7/1988 | |
| JP | 1-195309 A | 8/1989 | |
| JP | 3-502491 A | 6/1991 | |
| JP | 5-62573 A | 3/1993 | |
| JP | 7-55426 A | 3/1995 | |
| JP | 7-29405 U | 6/1995 | |
| JP | 7-191269 A | 7/1995 | |
| JP | 8-14874 A | 1/1996 | |
| JP | 8-93876 A | 4/1996 | |
| JP | 9-311034 A | 12/1997 | |
| JP | 10-137962 A | 5/1998 | |
| JP | 10-197215 A | 7/1998 | |
| JP | 10-213404 A | 8/1998 | |
| JP | 2000-136923 A | 5/2000 | |
| JP | 2000-146564 A | 5/2000 | |
| JP | 2002-22671 A | 1/2002 | |
| JP | 2002-148036 A | 5/2002 | |
| JP | 2003-139525 A | 5/2003 | |
| JP | 2003-329606 A | 11/2003 | |
| JP | 2004-176852 A | 6/2004 | |
| JP | 3105724 U | 11/2004 | |
| JP | 2005-315814 A | 11/2005 | |
| JP | 2005-331333 A | 12/2005 | |
| JP | 2006-153546 A | 6/2006 | |
| JP | 2006-156138 A | 6/2006 | |
| JP | 2006-229551 A | 8/2006 | |
| JP | 2006-234525 A | 9/2006 | |
| JP | 2007-57305 A | 3/2007 | |
| JP | 2007-71852 A | 3/2007 | |
| JP | 2007-248465 A | 9/2007 | |
| JP | 2007-292699 A | 11/2007 | |
| JP | 4230408 B2 | 2/2009 | |
| JP | 2010-164334 A | 7/2010 | |
| JP | 2011-2439 A | 1/2011 | |
| JP | 2011-13060 A | 1/2011 | |
| WO | 97/02480 A1 | 1/1997 | |
| WO | 2007051332 A2 | 5/2007 | |
| WO | 2009152851 A1 | 12/2009 | |
| WO | 2013/118918 A1 | 8/2013 | |

OTHER PUBLICATIONS

Notice of Allowance mailed Feb. 16, 2016 in co-pending U.S. Appl. No. 14/377,237.
Notice of Allowance mailed Mar. 1, 2016 in co-pending U.S. Appl. No. 14/377,237.
Notice of Allowance mailed Mar. 30, 2016 in co-pending U.S. Appl. No. 14/377,227.
Office Action mailed Mar. 25, 2015 in co-pending U.S. Appl. No. 14/377,225.
Notice of Allowance mailed Jul. 13, 2015 in co-pending U.S. Appl. No. 14/377,225.
European communication dated Oct. 7, 2015 in co-pending European patent application No. 13747245.2.
European communication dated Sep. 9, 2015 in co-pending European patent application No. 13746053.1
European communication dated Nov. 11, 2015 in co-pending European patent application No. 13746339.4.
European communication dated Oct. 8, 2015 in co-pending European patent application No. 13746993.8.
Office action mailed Dec. 1, 2015 in co-pending U.S. Appl. No. 14/377,227.
European communication dated Sep. 9, 2015 in co-pending European patent application No. 13746779.1.
Office action mailed Sep. 1, 2015 in co-pending U.S. Appl. No. 14/377,238.
European communication dated Sep. 4, 2015 in co-pending European patent application No. 13747139.7.
European communication dated Sep. 18, 2015 in co-pending European patent application No. 13746866.6.
European communication dated Sep. 14, 2015 in co-pending European patent application No. 13746596.9.

(56) References Cited

OTHER PUBLICATIONS

Notice of Allowance mailed Jun. 2, 2016 in co-pending U.S. Appl. No. 14/377,238.
Office action mailed Apr. 18, 2016 in co-pending U.S. Appl. No. 14/377,230.
Notice of Allowance mailed May 13, 2016 in co-pending U.S. Appl. No. 14/377,226.
International Search Report and Written Opinion mailed Apr. 23, 2013 in co-pending PCT application No. PCT/JP2013/053589.
International Preoiminary Report on Patentability mailed Aug. 21, 2014 in co-pending PCT application No. PCT/JP2013/053589.
International Search Report and Written Opinion mailed Apr. 2, 2013 in co-pending PCT application No. PCT/JP2013/053590.
International Preliminary Report on Patentability mailed Aug. 21, 2014 in co-pending PCT application No. PCT/JP2013/053590.
International Search Report and Written Opinion mailed Apr. 23, 2013 in corresponding PCT application No. PCT/JP2013/053591.
International Preliminary Report on Patentability mailed Aug. 21, 2014 in corresponding PCT application No. PCT/JP2013/053591.
International Search Report and Written Opinion mailed May 7, 2013 in co-pending PCT application No. PCT/JP2013/053592.
International Preliminary Report on Patentability mailed Aug. 21, 2014 in co-pending PCT application No. PCT/JP2013/053592.
International Search Report and Written Opinion mailed Mar. 12, 2013 in co-pending PCT application No. PCT/JP2013/053599.
International Preliminary Report on Patentability mailed Aug. 21, 2014 in co-pending PCT application No. PCT/JP2013/053599.
International Search Report and Written Opinion mailed May 7, 2013 in co-pending PCT application No. PCT/JP2013/053597.
International Preliminary Report on Patentability mailed Aug. 21, 2014 in co-pending PCT application No. PCT/JP2013/053597.
International Search Report and Written Opinion mailed Apr. 16, 2013 in co-pending PCT application No. PCT/JP2013/053598.
International Preliminary Report on Patentability mailed Aug. 21, 2014 in co-pending PCT application No. PCT/JP2013/053598.
International Search Report and Written Opinion mailed Apr. 2, 2013 in co-pending PCT application No. PCT/JP2013/053603.
International Preliminary Report on Patentability mailed Aug. 21, 2014 in co-pending PCT application No. PCT/JP2013/053603.
Notice of Allowance mailed Aug. 2, 2016 in co-pending U.S. Appl. No. 14/377,230.
Notice of Allowance mailed Oct. 3, 2016 in co-pending U.S. Appl. No. 14/377,234.
Final rejection mailed Dec. 29, 2015 in co-pending U.S. Appl. No. 14/377,238.
Office action mailed Dec. 30, 2015 in co-pending U.S. Appl. No. 14/377,226.

* cited by examiner

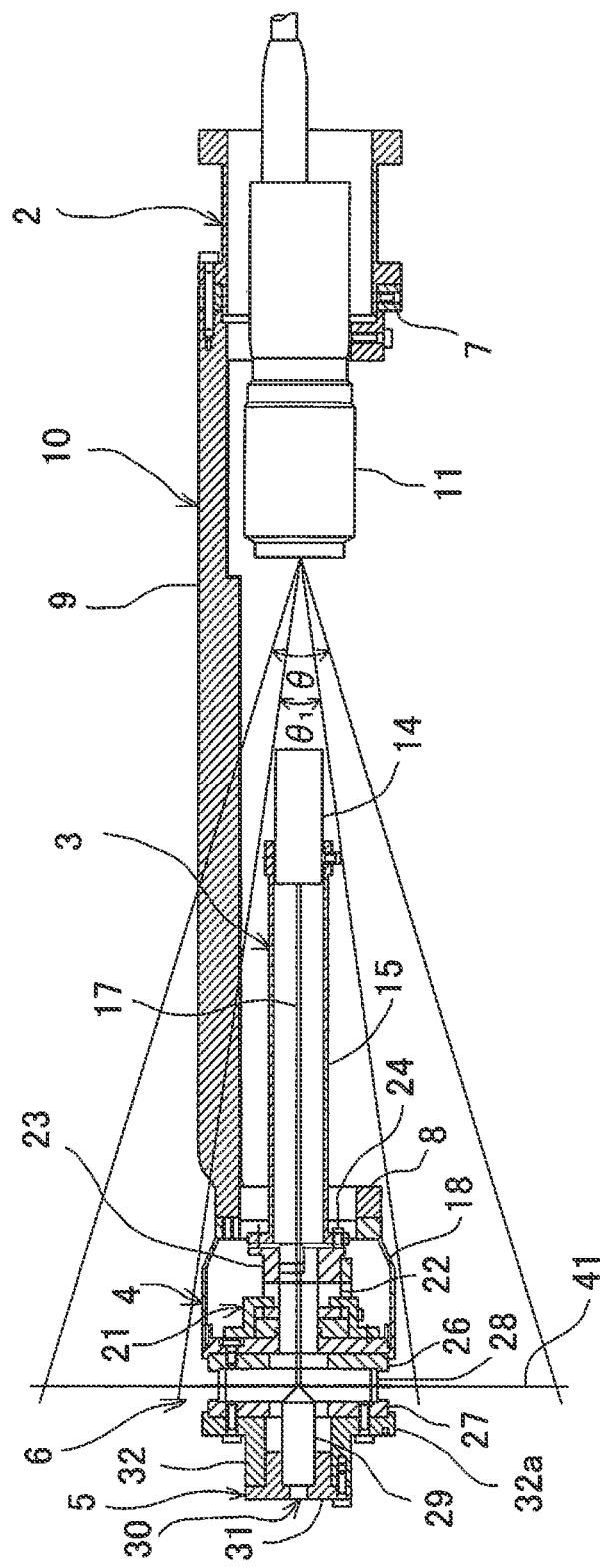
F I G . 2

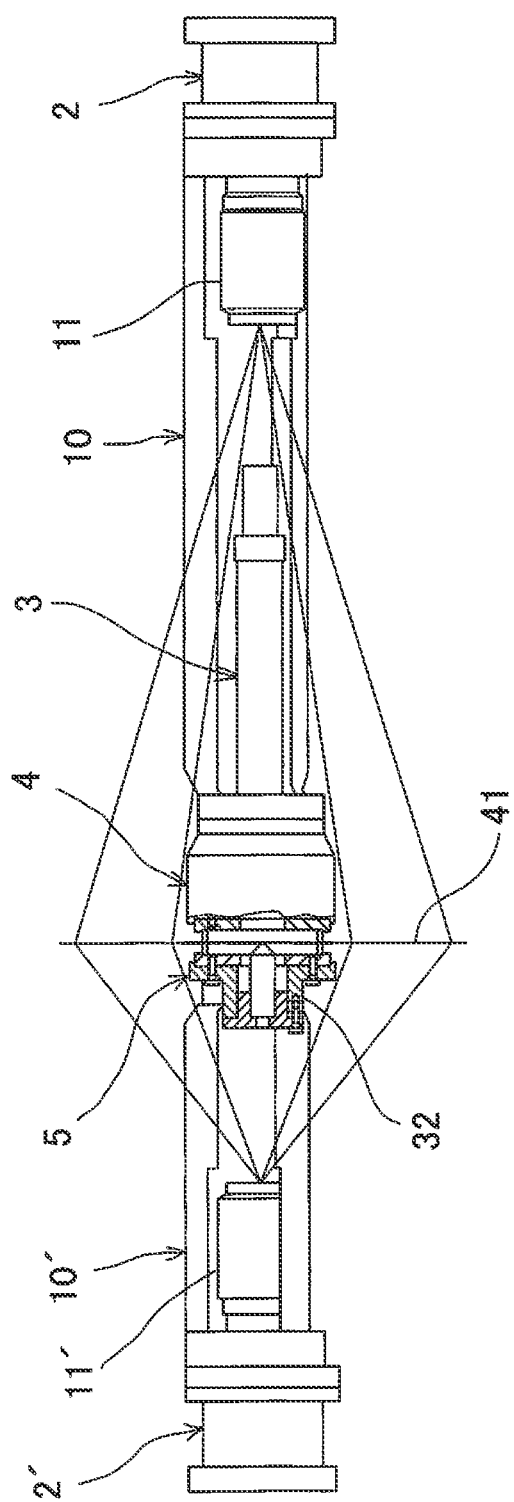

INNER DIAMETER MEASURING DEVICE

TECHNICAL FIELD

The present invention relates to an inner diameter measuring device for measuring an inner diameter or a shape of an inner surface of a cylindrical member, particularly to an inner diameter measuring device for measuring the shape of the inner surface on non-contact basis.

BACKGROUND ART

As a device for measuring an inner diameter of a cylindrical member on non-contact basis, a non-contact type inner diameter measuring device is known, by which a laser beam is projected in a total circumferential direction, and an optical ring is formed on an inner surface of the cylindrical member, and an image of the optical ring is picked up, and a shape and a diameter of the optical ring are measured from the image thus picked up.

Each of the Patent Document 1 and the Patent Document 2 discloses a non-contact type inner diameter measuring device, which projects a laser beam in a total circumferential direction and picks up an optical ring formed on the inner surface of the cylindrical member and measures the shape and the diameter of the optical ring from the image. In the inner diameter measuring device disclosed in each of the Patent Document 1 and the Patent Document 2, a cone mirror with a conical reflection surface is used as means for projecting a laser beam in a total circumferential direction, and by projecting the laser beam to a vertex of the cone mirror, the laser beam is reflected in a total circumferential direction. The laser beam diffused in a total circumferential direction is projected to the inner surface of the cylindrical member, and an optical ring is formed. This optical ring is picked up by an image pickup device, and a diameter, a shape, etc. of the inner surface are measured from an image acquired.

However, there are cases where various types of irregularities are existed on the inner surface of the cylindrical member such as a graded step protruding vertically from the inner surface, a curved portion protruding while being curved, a tapered part protruding in tapered manner, etc. By the conventional type inner diameter measuring device, it has been difficult to measure the diameter, the shape, etc. of the inner surface, in the graded step, the curved surface or the tapered part.

To solve the problems as described above, it is an object of the present invention to provide an inner diameter measuring device, which projects a laser beam in a total circumferential direction by means of a cone mirror, forms an optical ring on an inner surface of a cylindrical member, and measures an inner diameter and a shape of the cylindrical member based on the optical ring, wherein the inner diameter measuring device enables to measure even when the cylindrical member has irregularities on the inner surface.

CONVENTIONAL ART REFERENCES

Patent Document 1: JP-A-H10-197215
Patent Document 2: JP-A-2010-164334

DISCLOSURE OF THE INVENTION

The present invention relates to an inner diameter measuring device for measuring a shape of an inner surface of a cylindrical member, comprising an image pickup unit disposed on a base end side of a frame unit and for picking up an image of a forward end side, a cone mirror unit provided on a forward end side of the frame unit and having a cone mirror with a conical reflection surface at a forward end, and a laser beam emitting unit for emitting a laser beam toward a forward end of the cone mirror, wherein the cone mirror unit can be replaced by another cone mirror unit having a cone mirror with a different vertical angle to suit measuring condition.

Further, the present invention relates to an inner diameter measuring device, wherein the cone mirror unit is mounted by a fitting method, and by mounting the cone mirror unit, a center line of the cone mirror is configured to be made coincident with an optical axis of the laser beam emitting unit.

Further, the present invention relates to an inner diameter measuring device, wherein the cone mirror unit has a cone mirror with a vertical angle of right angle, and relates to an inner diameter measuring device, wherein the another cone mirror unit has a cone mirror with a vertical angle of acute angle or obtuse angle.

Furthermore, the present invention relates to an inner diameter measuring device, wherein another image pickup unit is provided on the cone mirror unit, and the another image pickup unit picks up an image of a base end side.

BRIEF DESCRIPTION OF THE DRAWINGS

FIG. 2 is a cross-sectional view of the inner diameter measuring device according to the embodiment of the present invention.

FIG. 4A shows a case where a cone mirror unit having a cone mirror with a vertical angle of acute angle is mounted, and FIG. 4B shows a case where a cone mirror unit having a cone mirror with a vertical angle of obtuse angle is mounted.

FIG. 6 is a cross-sectional view of an inner diameter measuring device according to another embodiment of the present invention.

BEST MODE FOR CARRYING OUT THE INVENTION

Description will be given below on an embodiment of the present invention by referring to the attached drawings.

Figure 1:
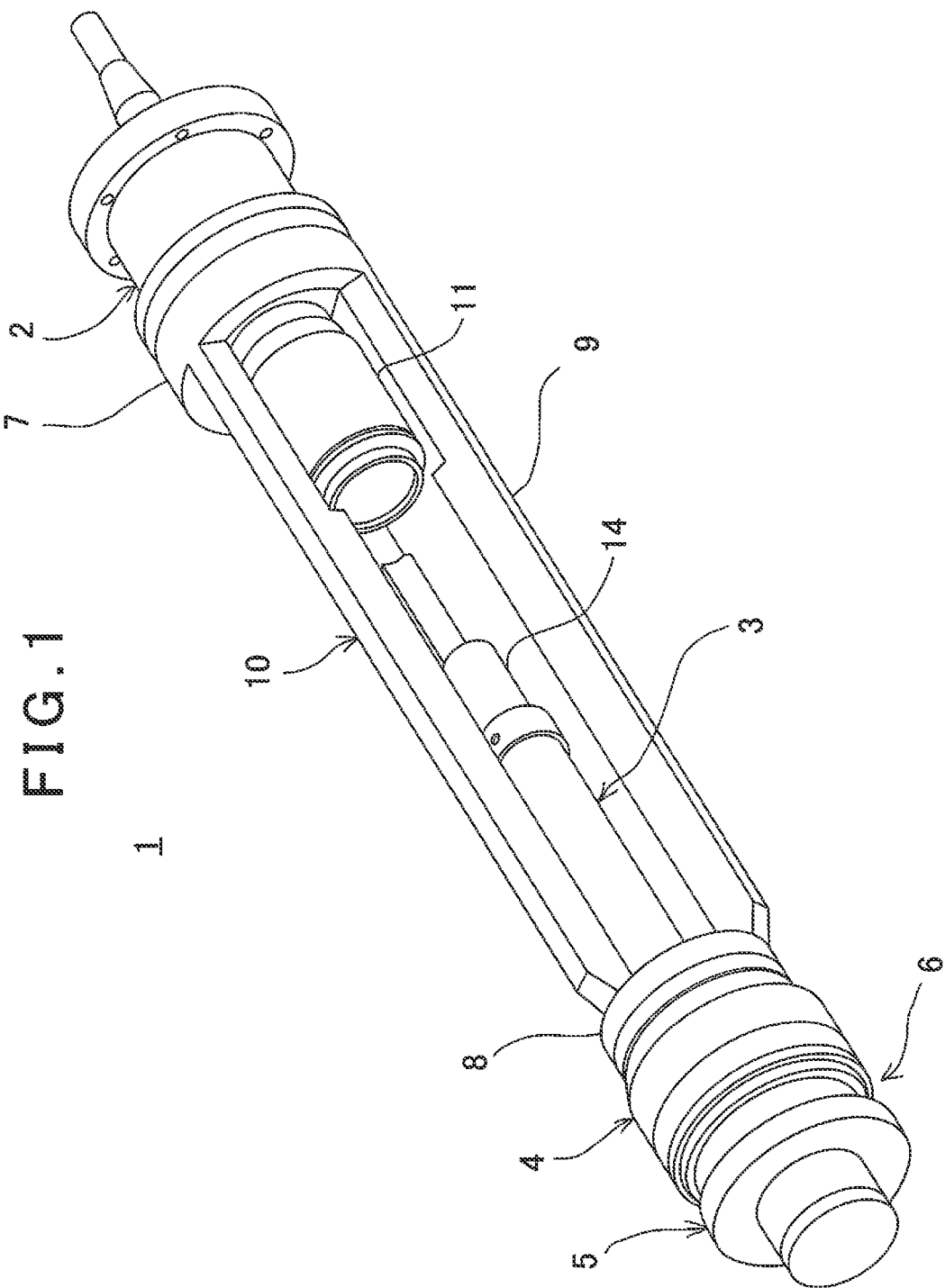
FIG. 1 is a perspective view of an inner diameter measuring device according to an embodiment of the present invention.
Figure 3:
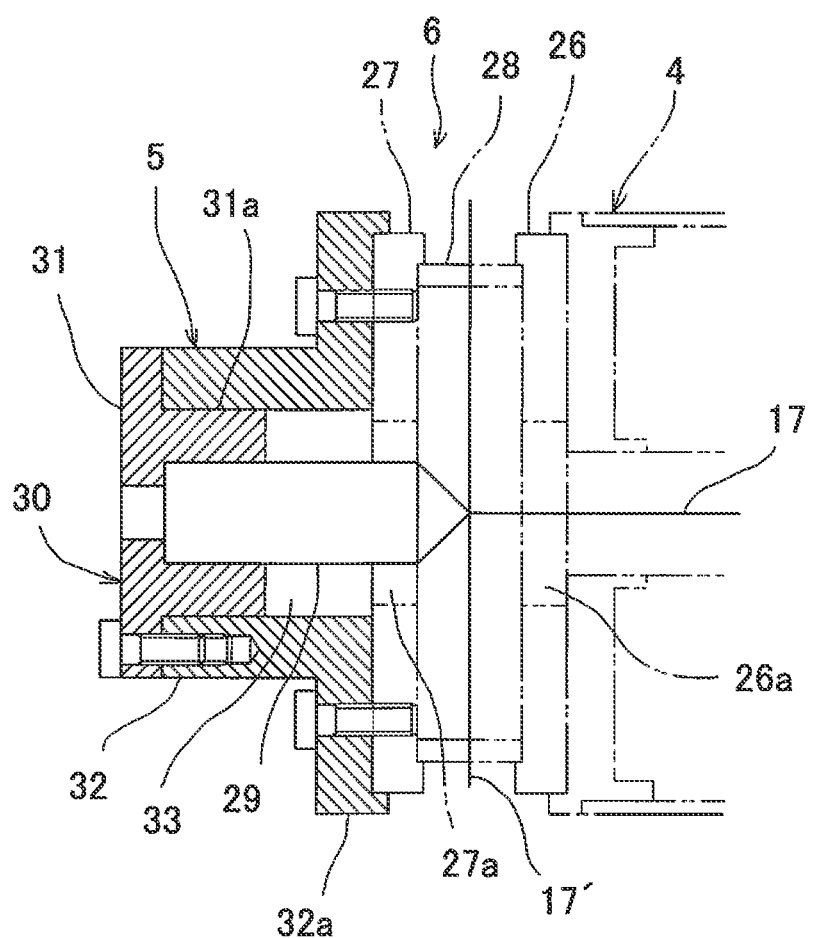
FIG. 3 is a cross-sectional view of a laser beam diffusing unit according to the embodiment of the present invention.

FIG. 1 to FIG. 3 each represents an inner diameter measuring device 1 according to an embodiment of the present invention. The inner diameter measuring device 1 primarily comprises an image pickup unit 2, a laser beam emitting unit 3, a core aligning unit 4, a laser beam diffusing unit 5, a light transmitting window 6, a frame unit 10, etc.

The frame unit 10 has such structural arrangement that a base end ring 7 and a forward end ring 8 are connected by three supporting pillars 9. The supporting pillars 9 are arranged on the same circumference with a predetermined distance from each other, e.g. at three equally divided positions. A space is formed at a central part of the frame unit 10, and the image pickup unit 2 and the laser beam emitting unit 3 are accommodated in the space. It is to be noted that there may be two or our supporting pillars 9 so far as the supporting pillars 9 can support the image pickup unit 2 and the laser beam diffusing unit 5 and no trouble is caused for image pickup by the image pickup unit 2.

The base end ring 7 and the forward end ring 8 are concentric to each other. That is, the base end ring 7 and the forward end ring 8 are arranged along a center line of the frame unit 10. On the base end ring 7, the image pickup unit 2 is mounted so as to penetrate through the base end ring 7. The image pickup unit 2 has a camera 11, and an optical axis of the image pickup unit 2, i.e. an optical axis of the camera 11, coincides with the center line of the frame unit 10.

The core aligning unit 4 is mounted on the forward end ring 8, and the laser beam emitting unit 3 is supported on the core aligning unit 1.

The laser beam emitting unit 3 has a laser emitter 14, which is held by a laser emitter holder 15, designed as a cylindrical member. A position and a posture of the laser beam emitting unit 3 can be adjusted by an adjusting mechanism unit 21 as to be described later. Under the condition that an adjustment of the position and the posture has been completed, an optical axis of the laser beam emitting unit 3, i.e. an optical axis of the laser emitter 14 is arranged to coincide with the center line of the frame unit 10 and with the optical axis of the image pickup unit 2.

The core aligning unit 4 has the adjusting mechanism unit 21 and a housing 18 to accommodate the adjusting mechanism unit 21.

The adjusting mechanism unit 21 has an X-axis slider 22, which can be displaced in a direction perpendicular to a paper surface in FIG. 2, and a Y-axis slider 23 disposed on the X-axis slider 22, which can be displaced in a direction in parallel to the paper surface in FIG. 2. The displacements of the X-axis slider 22 and the Y-axis slider 23 can be adjusted by adjusting screws (not shown).

On the Y-axis slider 23, the laser beam emitting unit 3 is fixed at three points by tilt adjusting screws 24. The tilt adjusting screw 24 has a set of a pushing screw and a pulling screw, and by adjusting a protruding amount of the pushing screw, a tilting of the optical axis of the laser beam, emitting unit 3 can be adjusted.

Therefore, the adjusting mechanism unit 21 has a function to displace the laser beam emitting unit 3 in two directions perpendicularly crossing the optical axis of the laser beam emitting unit 3 (in X-axis direction and in Y-axis direction) and also to adjust the tilting of the optical axis of the laser beam emitting unit 3.

The light transmitting window 6 is provided on the forward end side of the core aligning unit 4. The light transmitting window 6 has a first flange 26 on a base end side, where a round hole 26a is formed at a center, a second flange 27 on a forward end side, where a round hole 27a is formed at a center, and a total circumferential light transmitting window 28 sandwiched between the first flange 26 and the second flange 27. The total circumferential light transmitting window 28 is made of a transparent glass or a transparent synthetic resin.

The laser beam diffusing unit 5 is mounted on the second flange 27. Under the condition on that the laser beam diffusing unit 5 is mounted, the laser beam diffusing unit 5 is concentric to the core aligning unit 4, the frame unit 10 and the image pickup unit 2.

The laser beam diffusing unit 5 is constituted of the light transmitting window 6, a fixing flange 32 (to be described later) mounted on the light transmitting window 6, and a cone mirror unit 30 (to be described later) mounted on the fixing flange 32. The cone mirror unit 30 has a cone mirror 29 for reflecting a laser beam 17 projected from the laser emitter 14 in a total circumferential direction, and she light transmitting window 6 has the total circumferential light transmitting window 28, which allows a laser beam 17' reflected over total circumference by the cone mirror 29 to pass.

The cone mirror 29 has a forward end facing the laser emitter 14 in a conical shape, and a vertical angle of the cone is set to 90°, for instance. Also, a conical surface of the forward end is designed as a reflection surface.

The cone mirror 29 is unitized as held by a cone mirror holder 31 so that a center line of the cone mirror 29 coincides with an optical axis of the laser beam 17, and the cone mirror 29 and the cone mirror holder 31 make up together the cone mirror unit 30. The cone mirror holder 31 is arranged to be fixed on the second flange 27 via the fixing flange 32.

The cone mirror holder 31 has a fitting unit 31a. The fixing flange 32 has a flange portion 32a, and the flange portion 32a is fixed on the second flange 27 by a faucet joint method. An engaging hole 33 is penetrating in an axial direction on the fixing flange 32, and the fitting unit 31a is arranged to be fixed in the engaging hole 33 by the faucet joint method.

As described above, since the flange portion 32a and the second flange 27 are fixed by the faucet joint method, an accuracy of combination of the fixing flange 32 and the second flange 27 is determined by machining accuracy of the second flange 27 and the fixing flange 32. Since the fixing flange 32 and the cone mirror holder 31 are also fixed by the faucet joint method, an assembling accuracy is determined by machining accuracy of the fixing flange 32 and the cone mirror holder 31.

Therefore, under the condition that the cone mirror 29 and the cone mirror holder 31 are unitized, if a center line of the cone mirror holder 31 is made aligned with a center line of the cone mirror 29 with high accuracy, by simply assembling the cone mirror holder 31 on the fixing flange 32, the center line and the vertex of the cone mirror 29 coincides with the optical axis of the laser beam 17 without adjustment and a core aligning of the cone mirror 29 is accomplished.

Figure 4A:
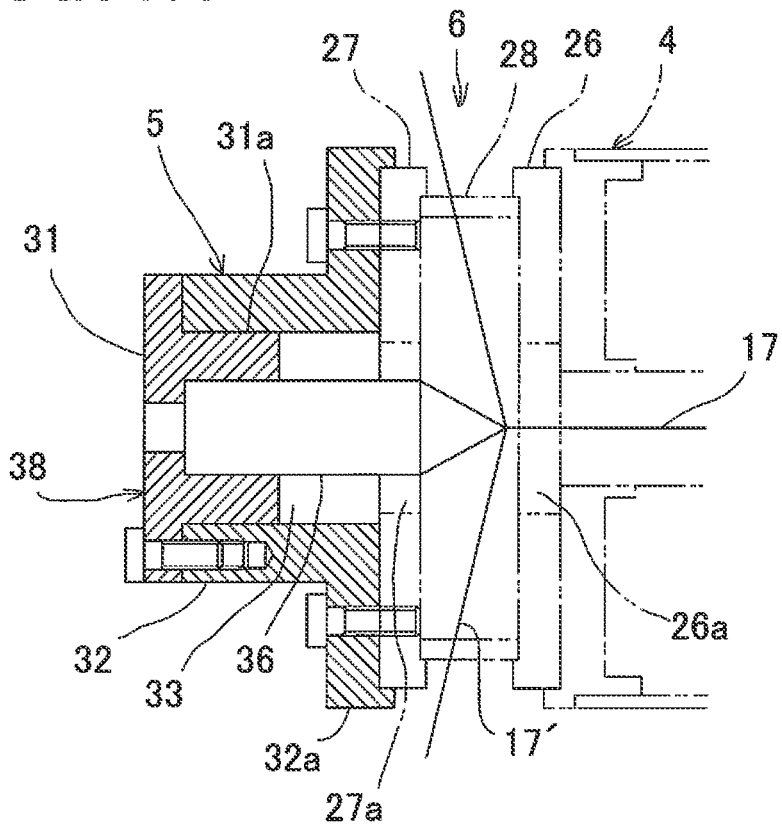
FIG. 4A and FIG. 4B each represents a cross-sectional view of the laser beam diffusing unit according to the embodiment of the present invention.
Figure 4B:
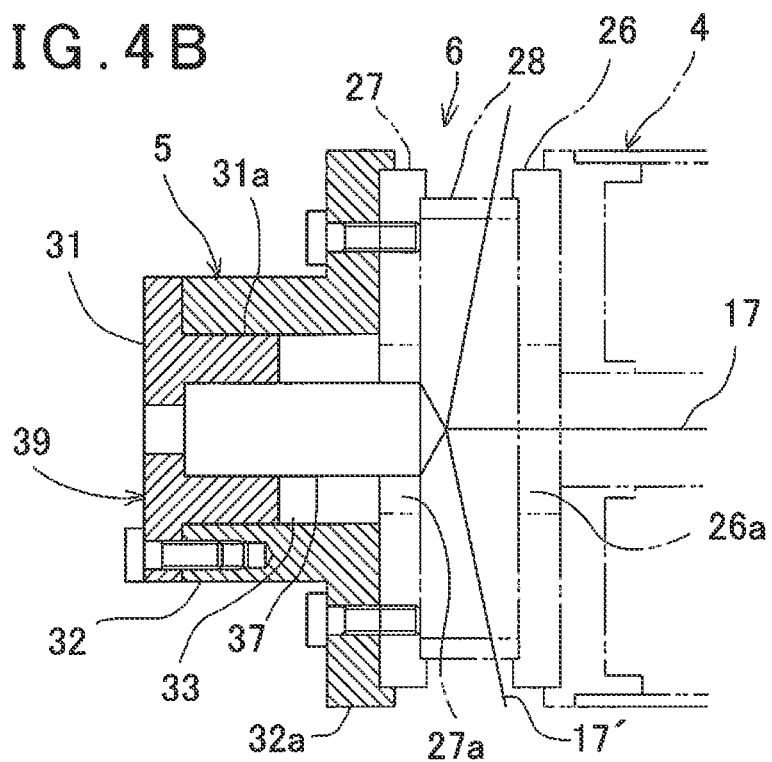

In the present embodiment, the cone mirror unit 30 is designed as replaceable. If cone mirror units having cone mirrors with different vertical angles, e.g. as shown in FIG. 4A and FIG. 4B, a cone mirror unit 38 and a cone mirror unit 39 having a cone mirror and a cone mirror 37 each with vertical angles of 60° and 120° are prepared, the cone mirror units 30, 38 and 39 can be adequately replaced to suit measuring condition. That is, the cone mirrors 29, 36, and 37 with vertical angle of right angle, acute angle, and obtuse angle can be used to suit measuring condition. The vertical angle is selected corresponding to the measuring condition and s not limited to 60° and 120°.

For instance, in a case where the cone mirror unit 30 having the cone mirror 29 with the vertical angle of right angle is mounted on the fixing flange 32, as shown in FIG. 3, the laser beam 17 projected from the laser emitter 14 is diffused and reflected on the conical surface of the cone mirror 29 in a direction perpendicularly crossing the center line of the cone mirror 29.

Also, in a case where the one mirror unit 38 having the cone mirror 36 with the vertical angle of 60° is mounted on the fixing flange 32 as shown in FIG. 4A, the laser beam 17 emitted from the laser emitter 14 is diffused and reflected toward the forward end side of the inner diameter measuring device rather than a forward end of the cone mirror 36 on a conical surface of the cone mirror 36.

In a case where the cone mirror unit 39 having the cone mirror 37 with the vertical angle of 120° is mounted on the fixing flange 32 as shown in FIG. 4B, the laser beam 17 emitted from the laser emitter 14 is diffused and reflected toward the base end side of the inner diameter measuring device 1 rather than a forward end of the cone mirror 37 on a conical surface of the cone mirror 37.

It is to be noted that in the present embodiment, the cone mirror 29 is held by the cone mirror holder 31 in advance and is unitized, while the cone mirror holder 31 holding the cone mirror 29 may be assembled on the fixing flange 32 in advance and be unitized. In this case, the cone mirror 29, the cone mirror holder 31, and the fixing flange 32 make up together the cone mirror unit 30. By simply assembling the fixing flange 32 on the second flange 27, the center line of the cone mirror 29 coincides with the optical axis of a laser beam 17.

Description will be given below on an operation of the inner diameter measuring device 1.

As a preparation for the measurement, under the condition that a center line of the light transmitting window 6 is aligned with the optical axis of the laser beam emitting unit 3 by the adjusting mechanism unit 21, the fixing flange 32 is mounted on the second flange 27. A cone mirror unit having a cone mirror with a predetermined vertical angle, e.g. the cone mirror unit 30 having the cone mirror 29, is mounted on the fixing flange 32. In this case, because the fixing flange 32 and the second flange 27, and also the cone mirror unit 30 and the fixing flange 32 are set by the faucet joint method, the center line of the cone mirror 29 is aligned with the center line of the light transmitting window 6 without adjustment, and the center line of the cone mirror 29 is arranged to coincide with the optical axis of the laser beam emitting unit 3.

After the inner diameter measuring device 1 is inserted into a cylindrical member such as a pipe or a hollow shaft not shown in the figure, and also is supported by a supporting device not shown in the figure, the laser beam 17 is projected from the laser emitter 14, and the laser beam 17 enters the vertex of the cone mirror 29.

The laser beam 17 is diffused and reflected on conical surface of the cone mirror 29 in a total circumferential direction and also in a direction perpendicularly crossing the center line of the cone mirror 29. The laser beam 17' thus reflected passes through the total circumferential light transmitting window 28 and is projected over total circumference.

The laser beam 17' is projected to the inner wall of the cylindrical member, and an optical ring 41 reflecting the shape of the inner wall is formed. The optical ring 41 is picked up by the image pickup unit 2, and an image data is acquired. Based on the image data of the optical ring 41 thus acquired, a diameter and a shape of the optical ring 41 are measured.

The maximum pickup field angle of the image pickup unit 2 is θ as shown in FIG. 2. The laser beam emitting unit 3, the core aligning unit 4, etc. serve as obstacles, and field angle of θ1 is turned to dead angle. Therefore, in the present embodiment, a range of field angle of θ to θ1 can be taken as an image.

Figure 5:
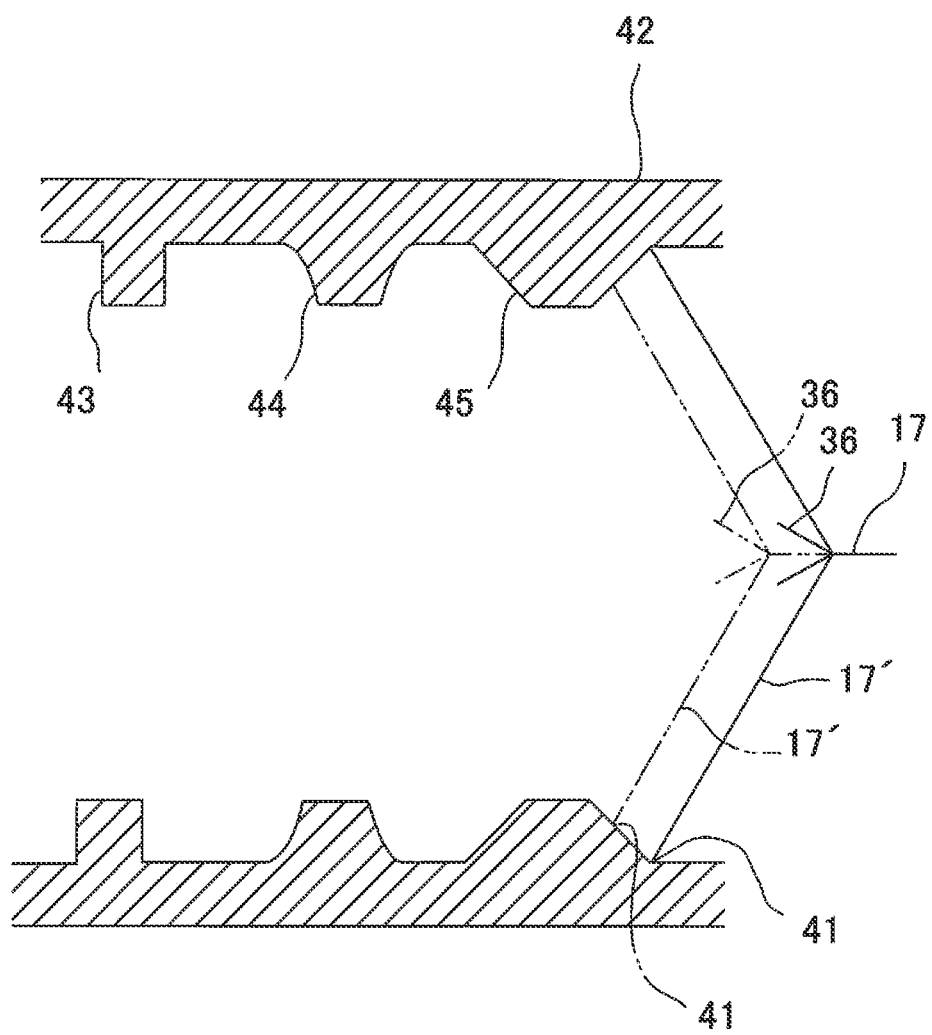
FIG. 5 is a schematical explanatory drawing of a cylindrical member according to the embodiment of the present invention.

In the measurement of the shape of the inner surface by the inner diameter measuring device 1 as described above, the shape of the inner surface of the cylindrical member 42 is not always constant as shown in FIG. 5, and there may be cases where various types of surface irregularities are present such as a graded step 43 protruding vertically from the inner surface, a portion with curved surface 44 protruding while being curved, a tapered portion 45 protruding in tapered manner, etc.

In a case where there are surface irregularities such as the graded step 43, the portion with curved surface 14 the tapered portion 45, etc., in particular, in a case of surface irregularities with a diameter rapidly changing, and when a laser beam 17 is diffused and reflected in a direction perpendicularly crossing the optical axis by the cone mirror 29, a measurement with high accuracy may be difficult to be performed such as a case where the formed optical ring 41 becomes discontinuous.

In this case, for instance, the cone mirror unit 30 is replaced by the cone mirror unit 38 (see FIG. 4A) having the cone mirror 36 with the vertical angle of 60°, i.e. acute angle. When the shape of the inner surface of the cylindrical member 42 is measured by using the cone mirror unit 38, the laser beam 17 emitted from the laser emitter 14 is diffused and reflected by the cone mirror 36 toward the forward end side of the inner diameter measuring device 1 rather than the forward end of the cone mirror 36 (see FIG. 5). Therefore, when the inner diameter measuring device 1 is moved forward and backward, even in a case where there are surface irregularities with the diameter rapidly changing, such as the graded step 43 or the curved surface 44, the optical ring 41 is made continuous without interrupting. As a result, it is possible to pick up the image of the optical ring 41 reliably and to measure the inner diameter and the shape of the inner surface of the cylindrical member 42 easily and with high accuracy.

FIG. 6 shows another embodiment. In the another embodiment, one more image pickup unit 2' is mounted on a laser beam diffusing unit 5 and an image of an optical ring 41 formed on an inner wall is arranged to be picked up from an opposite side of an image pickup unit 2. The image pickup unit 2' has a camera 11' and a frame unit 10', and a forward end of the frame unit 10' is mounted on a fixing flange 32.

By picking up an image of the optical ring 41 from an opposite side of a camera 11, a measurement can be performed even in a case where there are surface irregularities such as a graded step 43 (see FIG. 5), a curved surface 44 (see FIG. 5), a tapered portion 45 (see FIG. 5), etc. on an inner wall of a cylindrical member 42 (see FIG. 5), and the optical ring 41 thus formed comes into dead angle of the camera 11.

In this case, by replacing a cone mirror unit 30 (see FIG. 3) by a cone mirror unit 39 (see FIG. 4B) having a cone mirror 37 (see FIG. 4B) with the vertical angle of 120°, i.e. obtuse angle, a laser beam 17 is diffused and reflected by the cone mirror 37 toward the base end side of the inner diameter measuring device 1 rather than the forward end of the cone mirror 37. As a result, surface irregularities included in dead angle of the camera 11 can be measured by the camera 11' easily and with higher accuracy.

INDUSTRIAL APPLICABILITY

According to the present invention, an inner diameter measuring device for measuring a shape of an inner surface of a cylindrical member comprises an image pickup unit disposed on a base end side of a frame unit and for picking up an image of a forward end side, a cone mirror unit provided on a forward end side of the frame unit and having a cone mirror with a conical reflection surface at a forward end, and a laser beam emitting unit for emitting a laser beam toward a forward end of the cone mirror, wherein the cone mirror unit can be replaced by another cone mirror unit having a cone mirror with a different vertical angle to suit measuring condition. As a result, even in a case where there are surface irregularities on the inner surface of the cylindrical member, the laser beam can be projected on the inner surface of the cylindrical member without interruption and the shape of the inner surface of the cylindrical member can be measured easily and with higher accuracy.

LEGEND OF REFERENCE NUMERALS

1 Inner diameter measuring device
2 Image pickup unit
3 Laser beam emitting unit
4 Core aligning unit
5 Laser beam diffusing unit
6 Light transmitting window
14 Laser emitter
17 Laser beam
21 Adjusting mechanism unit
29 Cone mirror
30 Cone mirror unit
31 Cone mirror holder
32 Fixing flange
33 Engaging hole
36 Cone mirror
37 Cone mirror
38 Cone mirror unit
39 Cone mirror unit
41 Optical ring

The invention claimed is:

1. An inner diameter measuring device for measuring a shape of an inner surface of a cylindrical member, comprising an image pickup unit disposed on a base end side of a frame unit and for picking up an image of a forward end side, two or more cone mirror units provided on a forward end side of said frame unit, having a cone mirror with a conical reflection surface and a different vertical angle at a forward end, and a laser beam emitting unit for emitting a laser beam toward a forward end of said cone mirror, wherein said cone mirror unit is comprised of said cone mirror having a vertical angle corresponding to a measuring condition and a cone mirror holder which holds said cone mirror and has a fitting unit which is capable of fitting to the forward end side of said frame unit, wherein said cone mirror is mounted by fitting of said fitting unit on the forward end side of said frame unit, a center line of said cone mirror coincides with a center line of said laser beam emitting unit by the fitting of said fitting unit, and said laser beam is reflected at a predetermined angle with respect to the center line of said laser beam emitting unit by said cone mirror unit.

2. An inner diameter measuring device according to claim 1, wherein said cone mirror unit has a cone mirror with a vertical angle of right angle.

3. An inner diameter measuring device according to claim 1, wherein another cone mirror unit has a cone mirror with a vertical angle of acute angle or obtuse angle.

4. An inner diameter measuring device according to claim 1, wherein another image pickup unit is provided on said cone mirror unit, and said another image pickup unit picks up an image of a base end side.

5. An inner diameter measuring device according to claim 2, wherein another image pickup unit is provided on said cone mirror unit, and said another image pickup unit picks up an image of a base end side.

* * * * *